US010996222B2

(12) United States Patent
Lawrence et al.

(10) Patent No.: US 10,996,222 B2
(45) Date of Patent: May 4, 2021

(54) ENZYME-LINKED IMMUNOSORBENT ASSAY (ELISA) FOR THE DETECTION OF ANTI-MYCOPLASMA HYORHINIS IGG IN SWINE SERUM

(71) Applicant: BOEHRINGER INGELHEIM ANIMAL HEALTH USA INC., Duluth, GA (US)

(72) Inventors: Paulraj Lawrence, Arden Hills, MN (US); Russell F. Bey, Alexandria, MN (US); Mike Stoll, Worthington, MN (US); Eric Bumgardner, Worthington, MN (US); Douglas Stine, Overland Park, KS (US)

(73) Assignee: Boehringer Ingelheim Animal Health USA Inc., Duluth, GA (US)

( * ) Notice: Subject to any disclaimer, the term of this patent is extended or adjusted under 35 U.S.C. 154(b) by 841 days.

(21) Appl. No.: 15/533,345

(22) PCT Filed: Dec. 7, 2015

(86) PCT No.: PCT/US2015/064342
§ 371 (c)(1),
(2) Date: Jun. 5, 2017

(87) PCT Pub. No.: WO2016/090383
PCT Pub. Date: Jun. 9, 2016

(65) Prior Publication Data
US 2017/0363622 A1    Dec. 21, 2017

Related U.S. Application Data

(60) Provisional application No. 62/088,417, filed on Dec. 5, 2014.

(51) Int. Cl.
*G01N 33/569* (2006.01)
*C07K 14/30* (2006.01)

(52) U.S. Cl.
CPC ....... *G01N 33/56933* (2013.01); *C07K 14/30* (2013.01)

(58) Field of Classification Search
CPC . C07K 14/30; G01N 33/56933; G01N 33/569
See application file for complete search history.

(56) References Cited

U.S. PATENT DOCUMENTS 4,708,871 A    11/1987 Geysen

FOREIGN PATENT DOCUMENTS

EP    308265 A2    3/1989

OTHER PUBLICATIONS

Urbanek et al: "Detection of antibodies directed at M. hyorhinis p. 37 in the serum of men with newly diagnosed prostate cancer",BMC Cancer, Biomed Central, London, GB.vol. 11, No. 1, Jun. 10, 2011 (Jun. 10, 2011), p. 233, (Year: 2011).*

(Continued)

*Primary Examiner* — Jana A Hines
(74) *Attorney, Agent, or Firm* — Steffan Finnegan (57) ABSTRACT

This disclosure presents an Enzyme-Linked Immunosorbent Assay (ELISA) for the selective detection of anti-*Mycoplasma hyorhinis* IgG in porcine serum, which may contain antibodies specific to multiple other *Mycoplasma* spp.

4 Claims, 6 Drawing Sheets

Specification includes a Sequence Listing.

(56) References Cited

OTHER PUBLICATIONS

Urbanek: "Detection of antibodies directed at M. hyorhinis p37 in the serum of men with newly diagnosed prostate cancer" BMC Cancer Biomed Central, London, GB vol. 11, No. 1~ Jun. 10, 2011 (Jun. 10, 2011) p. 233, XP021102349. Cited in ISR.

Dudler: "A mycoplasma high-affinity transport system and the in vitro invasiveness of mouse sarcoma cells." EMBO Journal, vol. 7, Jan. 1, 1988 (Jan. 1, 1988), p. 3963, XP055249270. Cited in ISR as an "A" ref.

Armstrong CH; Sands-Freeman L; Freeman MJ: "Serological, pathological, and cultural evaluations of swine infected experimentally with Mycoplasma flocculare", Can J Vet Res, vol. 51, 1987, pp. 185-188.

Citti C; Kim MF; Wise KS: "Elongated versions of VLP surface lipoproteins protect Mycoplasma hyorhinis escape variants from growth-inhibiting host antibodies", Infect Immun, vol. 65, pp. 1773-1785.

Dudler R; Schmidhauser C; Parish RW et al.: "A mycoplasma high-affinity transport system and the in vitro invasiveness of mouse sarcoma cells", EMBO J, vol. 7, 1988, pp. 3963-3970.

Friis NF; Ahrens P; Larsen H: "Mycoplasma hyosynoviae isolation from the upper respiratory tract and tonsils of pigs", Acta Vet Scand, vol. 32, 1991, pp. 425-429.

Gois M; Kuksa F: "Intranasal infection of gnotobiotic piglets with Mycoplasma hyorhinis: Differences in virulence of the strains and influence of age on the development of infection", Zentralbl Veterinarmed B, vol. 21, 1974, pp. 352-361.

Gomes Neto JC; Gauger PC; Strait EL et al.: "Mycoplasma-associated arthritis: Critical points for diagnosis", J Swine Health Prod, vol. 20, 2012, pp. 82-86.

Gong M; Meng L; Beihai J et al.: "p37 from Mycoplasma hyorhinis promotes cancer cell invasiveness and metastasis through activation of MMP- and followed by phosphorylation of EGFR", Mol Cancer Ther, vol. 7, 2008, pp. 530-537.

Hagedorn-Olsen T; Nielsen NC; Friis NF; Nielsen J: "Progression of Mycoplasma hyosynoviae infection in three pig herds. Development of tonsillar carrier state, arthritis, and antibodies in serum and synovial fluid in pigs from birth to slaughter", Zentralbl Veterinarmed a, vol. 46, 1999, pp. 555-564.

Hansen MS; Pors SE; Jensen HE et al.: "An investigation of the pathology and pathogens associated with porcine respiratory disease complex in Denmark", J Comp Pathol, vol. 143, 2010, pp. 120-131.

Ketcham CM; Anai S; Reutzel R et al.: "p induces tumor invasiveness", Mol Cancer Ther, vol. 4, 2005, pp. 1031-1038.

Kim B; Lee K; Han K et al.: "Development of in situ hybridization for the detection of Mycoplasma hyorhinis in formalin-fixed paraffin-embedded tissues from naturally infected pigs with polyserositis", J Vet Med Sci, vol. 72, pp. 1225-1227.

Kobisch M; Friis NF: "Swine mycoplasmoses", Rev Sci Tech, vol. 15, 1996, pp. 1569-1605.

Liu W; Fang L; Li M et al.: "Comparative genomics of Mycoplasma: Analysis of conserved essential genes and diversity of the pan-genome", PLOS One, vol. 7, 2012, pp. E35698.

Minion FC: "Molecular pathogenesis of mycoplasma animal respiratory pathogens", Front Biosci, vol. 7, 2002, pp. 1410-1422.

Namiki K; Goodison S; Porvasnik S et al.: "Persistent exposure to Mycoplasma induces malignant transformation of human prostate cells", PLOS One, vol. 4, 2009, pp. E6872.

Nielsen EO; Lauritsen KT; Friis NF et al.: "Use of a novel serum ELISA method and the tonsil-carrier state for evaluation of Mycoplasma hyosynoviae distributions in pig herds with or without clinical arthritis", Vet Microbiol, vol. 111, 2005, pp. 41-45.

Palzer A; Ritzmann M; Wolf G; Heinritzi K: "Associations between pathogens in healthy pigs and pigs with pneumonia", Vet Rec, vol. 162, 2008, pp. 267-271.

Razin S; Hayflick L: "Highlights of mycoplasma research—An historical perspective", Biologicals, vol. 38, 2010, pp. 183-190.

Rosengarten R; Wise KS: "Phenotypic switching in mycoplasmas: phase variation of diverse surface lipoproteins", Science, vol. 247, 1990, pp. 315-318.

Rosengarten R; Wise KS: "The VLP system of Mycoplasma hyorhinis: Combinatorial expression of distinct size variant lipoproteins generating high frequency surface antigenic variation", J Bacteriol, vol. 173, 1991, pp. 4782-4793.

Sippel KH; Robbins AH; Reutzel R et al.: "Structural insights into the extracytoplasmic thiamine-binding lipoprotein p of Mycoplasma hyorhinis", J Bacteriol, vol. 191, 2009, pp. 2585-2592.

Stephen F; Altschul TL; Madden AA et al.: "Gapped BLAST and PSI-BLAST: a new generation of protein database search programs", Nucleic Acids Res, vol. 25, 1997, pp. 3389-3402.

Teh HS; Ho M; Williams LD: "Suppression of cytotoxic responses by a supernatant factor derived from Mycoplasma hyorhinis-infected mammalian cell lines", Infect Immun, vol. 56, 1988, pp. 197-203.

Yang H; Qu L; Chen L et al.: "Mycoplasma hyorhinis infection in gastric carcinoma and its effects on the malignant phenotypes of gastric cancer cells", BMC Gastroenterol, vol. 10, 2010, pp. 132-139.

* cited by examiner

P37rec = SEQ ID NO:5

```
10-3162-1    ----------------------------------------------------------LLK
11-3945-1    ----------------------------------------------------------LLK
11-0731-1    ----------------------------------------------------------LLK
10-1118-4    ----------------------------------------------------------LLK
09-4107-1    ----------------------------------------------------------LLK
10-2286-1    ----------------------------------------------------------LLK
10-1625-1    ----------------------------------------------------------LLK
12-4130-1    ----------------------------------------------------------LLK
12-3129-1    ----------------------------------------------------------LLK
13-00490     ----------------------------------------------------------LLK
12-4153-1    ----------------------------------------------------------LLK
12-1416-1    ----------------------------------------------------------LLK
12-2665-1    ----------------------------------------------------------LLK
12-1973-2    ----------------------------------------------------------LLK
11-4503-1    ----------------------------------------------------------LLK
12-1276-1    ----------------------------------------------------------LLK
p37rec       MHHHHHHSSGLVPRGSGMKETAAAKFKRQHMDSPDLGTDDDDKMKASAVDGPGIRSNMLK 10-3162-1    KFKNFILFSSIFSPIAFAISCSNTGVVKQEDVSVSQGQWDKSITFGVSEAWLNKKKGDKEVNKEVI
11-3945-1    KFKNFILFSSIFSPIAFAISCSNTGVVKQEDVSVSQGQWDKSITFGVSEAWLNKKKGDKEVNKEVI
11-0731-1    KFKNFILFSSIFSPIAFAISCSNTGVVKQEDVSVSQGQWDKSITFGVSEAWLNKKKGDKEVNKEVI
10-1118-4    KFKNFILFSSIFSPIAFAISCSNTGVVKQEDVSVSQGQWDKSITFGVSEAWLNKKKGDKEVNKEVI
09-4107-1    KFKNFILFSSIFSPIAFAISCSNTGVVKQEDVSVSQGQWDKSITFGVSEAWLNKKKGDKEVNKEVI
10-2286-1    KFKNFILFSSIFSPIAFAISCSNTGVVKQEDVSVSQGQWDKSITFGVSEAWLNKKKGDKEVNKEVI
10-1625-1    KFKNFILFSSIFSPIAFAISCSNTGVVKQEDVSVSQGQWDKSITFGVSEAWLNKKKGDKEVNKEVI
12-4130-1    KFKNFILFSSIFSPIAFAISCSNTGVVKQEDVSVSQGQWDKSITFGVSEAWLNKKKGDKEVNKEVI
12-3129-1    KFKNFILFSSIFSPIAFAISCSNTGVVKQEDVSVSQGQWDKSITFGVSEAWLNKKKGDKEVNKEVI
13-00490     KFKNFILFSSIFSPIAFAISCSNTGVVKQEDVSVSQGQWDKSITFGVSEAWLNKKKGDKEVNKEVI
12-4153-1    KFKNFILFSSIFSPIAFAISCSNTGVVKQEDVSVSQGQWDKSITFGVSEAWLNKKKGDKEVNKEVI
12-1416-1    KFKNFILFSSIFSPIAFAISCSNTGVVKQEDVSVSQGQWDKSITFGVSEAWLNKKKGDKEVNKEVI
12-2665-1    KFKNFILFSSIFSPIAFAISCSNTGVVKQEDVSVSQGQWDKSITFGVSEAWLNKKKGDKEVNKEVI
12-1973-2    KFKNFILFSSIFSPIAFAISCSNTGVVKQEDVSVSQGQWDKSITFGVSEAWLNKKKGDKEVNKEVI
11-4503-1    KFKNFILFSSIFSPIAFAISCSNTGVVKQEDVSVSQGQWDKSITFGVSEAWLNKKKGDKEVNKEVI
12-1276-1    KFKNFILFSSIFSPIAFAISCSNTGVVKQEDVSVSQGQWDKSITFGVSEAWLNKKKGDKEVNKEVI
p37rec       KLKNFILFSSIFSPIAFAISCSNTGVVKQEDVSVSQGQWDKSITFGVSEAWLNKKKGEKVNKEVI
```

*FIG. 6*

```
10-3162-1  NTFLENFKKEFNKLKNANDKTKNFDDVDFKVTPIQDSTVLLNNLSTDNPELDFGINASGKLVEFL
11-3945-1  NTFLENFKKEFNKLKNANDKTKNFDDVDFKVTPIQDSTVLLNNLSTDNPELDFGINASGKLVEFL
11-0731-1  NTFLENFKKEFNKLKNANDKTKNFDDVDFKVTPIQDSTVLLNNLSTDNPELDFGINASGKLVEFL
10-1118-4  NTFLENFKKEFNKLKNANDKTKNFDDVDFKVTPIQDSTVLLNNLSTDNPELDFGINASGKLVEFL
09-4107-1  NTFLENFKKEFNKLKNANDKTKNFDDVDFKVTPIQDSTVLLNNLSTDNPELDFGINASGKLVEFL
10-2286-1  NTFLENFKKEFNKLKNANDKTKNFDDVDFKVTPIQDSTVLLNNLSTDNPELDFGINASGKLVEFL
10-1625-1  NTFLENFKKEFNKLKNANDKTKNFDDVDFKVTPIQDSTVLLNNLSTDNPELDFGINASGKLVEFL
12-4130-1  NTFLENFKKEFNKLKNANDKTKNFDDVDFKVTPIQDSTVLLNNLSTDNPELDFGINASGKLVEFL
12-3129-1  NTFLENFKKEFNKLKNANDKTKNFDDVDFKVTPIQDSTVLLNNLSTDNPELDFGINASGKLVEFL
13-00490   NTFLENFKKEFNKLKNANDKTKNFDDVDFKVTPIQDSTVLLNNLSTDNPELDFGINASGKLVEFL
12-4153-1  NTFLENFKKEFNKLKNANDKTKNFDDVDFKVTPIQDSTVLLNNLSTDNPELDFGINASGKLVEFL
12-1416-1  NTFLENFKKEFNKLKNANDKTKNFDDVDFKVTPIQDSTVLLNNLSTDNPELDFGINASGKLVEFL
12-2665-1  NTFLENFKKEFNKLKNANDKTKNFDDVDFKVTPIQDSTVLLNNLSTDNPELDFGINASGKLVEFL
12-1973-2  NTFLENFKKEFNKLKNANDKTKNFDDVDFKVTPIQDSTVLLNNLSTDNPELDFGINASGKLVEFL
11-4503-1  NTFLENFKKEFNKLKNANDKTKNFDDVDFKVTPIQDSTVLLNNLSTDNPELDFGINASGKLVEFL
12-1276-1  NTFLENFKKEFNKLKNANDKTKNFDDVDFKVTPIQDSTVLLNNLSTDNPELDFGINASGKLVEFL
p37rec     NTFLENFKKEFNKLKNANDKTKNFDDVDFKVTPIQDFTVLLNNLSTDNPELDFGINASGKLVEFL 10-3162-1  KNNPGIITPALETTTNSFVFDKEKDKFYVDGTDSDPLVKIAKEINKIFVETPYASWTDENHKWNG
11-3945-1  KNNPGIITPALETTTNSFVFDKEKDKFYVDGTDSDPLVKIAKEINKIFVETPYASWTDENHKWNG
11-0731-1  KNNPGIITPALETTTNSFVFDKEKDKFYVDGTDSDPLVKIAKEINKIFVETPYASWTDENHKWNG
10-1118-4  KNNPGIITPALETTTNSFVFDKEKDKFYVDGTDSDPLVKIAKEINKIFVETPYASWTDENHKWNG
09-4107-1  KNNPGIITPALETTTNSFVFDKEKDKFYVDGTDSDPLVKIAKEINKIFVETPYASWTDENHKWNG
10-2286-1  KNNPGIITPALETTTNSFVFDKEKDKFYVDGTDSDPLVKIAKEINKIFVETPYASWTDENHKWNG
10-1625-1  KNNPGIITPALETTTNSFVFDKEKDKFYVDGTDSDPLVKIAKEINKIFVETPYASWTDENHKWNG
12-4130-1  KNNPGIITPALETTTNSFVFDKEKDKFYVDGTDSDPLVKIAKEINKIFVETPYASWTDENHKWNG
12-3129-1  KNNPGIITPALETTTNSFVFDKEKDKFYVDGTDSDPLVKIAKEINKIFVETPYASWTDENHKWNG
13-00490   KNNPGIITPALETTTNSFVFDKEKDKFYVDGTDSDPLVKIAKEINKIFVETPYASWTDENHKWNG
12-4153-1  KNNPGIITPALETTTNSFVFDKEKDKFYVDGTDSDPLVKIAKEINKIFVETPYASWTDENHKWNG
12-1416-1  KNNPGIITPALETTTNSFVFDKEKDKFYVDGTDSDPLVKIAKEINKIFVETPYASWTDENHKWNG
12-2665-1  KNNPGIITPALETTTNSFVFDKEKDKFYVDGTDSDPLVKIAKEINKIFVETPYASWTDENHKWNG
12-1973-2  KNNPGIITPALETTTNSFVFDKEKDKFYVDGTDSDPLVKIAKEINKIFVETPYASWTDENHKWNG
11-4503-1  KNNPGIITPALETTTNSFVFDKEKDKFYVDGKDSDPLVKIAKEINKIFVETPYASWTDENHKWNG
12-1276-1  KNNPGIITPALETTTNSFVFDKEKDKFYVDGKDSDPLVKIAKEINKIFVETPYASWTDENHKWNG
p37rec     KNNPGIITPALETTTNSFVFDKEKDKFYVDGTDSDPLVKIAKEINKIFVETPYASWTDENHKWNG 10-3162-1  NVYQSVYDPTVQANFYRGMIWIKGNDETLAKIKKAWNDKDWNTFRNFGILHGKDNSSSKFKL
11-3945-1  NVYQSVYDPTVQANFYRGMIWIKGNDETLAKIKKAWNDKDWNTFRNFGILHGKDNSSSKFKL
11-0731-1  NVYQSVYDPTVQANFYRGMIWIKGNDETLAKIKKAWNDKDWNTFRNFGILHGKDNSSSKFKL
10-1118-4  NVYQSVYDPTVQANFYRGMIWIKGNDETLAKIKKAWNDKDWNTFRNFGILHGKDNSSSKFKL
09-4107-1  NVYQSVYDPTVQANFYRGMIWIKGNDETLAKIKKAWNDKDWNTFRNFGILHGKDNSSSKFKL
10-2286-1  NVYQSVYDPTVQANFYRGMIWIKGNDETLAKIKKAWNDKDWNTFRNFGILHGKDNSSSKFKL
10-1625-1  NVYQSVYDPTVQANFYRGMIWIKGNDETLAKIKKAWNDKDWNTFRNFGILHGKDNSSSKFKL
12-4130-1  NVYQSVYDPTVQANFYRGMIWIKGNDETLAKIKKAWNDKDWNTFRNFGILHGKDNSSSKFKL
12-3129-1  NVYQSVYDPTVQANFYRGMIWIKGNDETLAKIKKAWNDKDWNTFRNFGILHGKDNSSSKFKL
13-00490   NVYQSVYDPTVQANFYRGMIWIKGNDETLAKIKKAWNDKDWNTFRNFGILHGKDNSSSKFKL
12-4153-1  NVYQSVYDPTVQANFYRGMIWIKGNDETLAKIKKAWNDKDWNTFRNFGILHGKDNSSSKFKL
12-1416-1  NVYQSVYDPTVQANFYRGMIWIKGNDETLAKIKKAWNDKDWNTFRNFGILHGKDNSSSKFKL
12-2665-1  NVYQSVYDPTVQANFYRGMIWIKGNDETLAKIKKAWNDKDWNTFRNFGILHGKDNSSSKFKL
12-1973-2  NVYQSVYDPTVQANFYRGMIWIKGNDETLAKIKKAWNDKDWNTFRNFGILHGKDNSSSKFKL
11-4503-1  NVYQSVYDPTVQANFYRGMIWIKGNDETLAKIKKAWNDKDWNTFRNFGILHGKDNSSSKFKL
12-1276-1  NVYQSVYDPTVQANFYRGMIWIKGNDETLAKIKKAWNDKDWNTFRNFGILHGKDNSSSKFKL
p37rec     NVYQSVYDPTVQANFYRGMIWIKGNDETLAKIKKAWNDKDWNTFRNFGILHGKDNSFSKFKL
```

*FIG. 6 (Cont'd)*

```
10-3162-1  EETILKNHFQNKFTTLNEDRSAHPNAYKQKSADTLGTLDDFHIAFSEEGSFAWTHNKSATKPFET
11-3945-1  EETILKNHFQNKFTTLNEDRSAHPNAYKQKSADTLGTLDDFHIAFSEEGSFAWTHNKSATKPFET
11-0731-1  EETILKNHFQNKFTTLNEDRSAHPNAYKQKSADTLGTLDDFHIAFSEEGSFAWTHNKSATKPFET
10-1118-4  EETILKNHFQNKFTTLNEDRSAHPNAYKQKSADTLGTLDDFHIAFSEEGSFAWTHNKSATKPFET
09-4107-1  EETILKNHFQNKFTTLNEDRSAHPNAYKQKSADTLGTLDDFHIAFSEEGSFAWTHNKSATKPFET
10-2286-1  EETILKNHFQNKFTTLNEDRSAHPNAYKQKSADTLGTLDDFHIAFSEEGSFAWTHNKSATKPFET
10-1625-1  EETILKNHFQNKFTTLNEDRSAHPNAYKQKSADTLGTLDDFHIAFSEEGSFAWTHNKSATKPFET
12-4130-1  EETILKNHFQNKFTTLNEDRSAHPNAYKQKSADTLGTLDDFHIAFSEEGSFAWTHNKSATKPFET
12-3129-1  EETILKNHFQNKFTTLNEDRSAHPNAYKQKSADTLGTLDDFHIAFSEEGSFAWTHNKSATKPFET
13-00490   EETILKNHFQNKFTTLNEDRSAHPNAYKQKSADTLGTLDDFHIAFSEEGSFAWTHNKSATKPFET
12-4153-1  EETILKNHFQNKFTTLNEDRSAHPNAYKQKSADTLGTLDDFHIAFSEEGSFAWTHNKSATKPFET
12-1416-1  EETILKNHFQNKFTTLNEDRSAHPNAYKQKSADTLGTLDDFHIAFSEEGSFAWTHNKSATKPFET
12-2665-1  EETILKNHFQNKFTTLNEDRSAHPNAYKQKSADTLGTLDDFHIAFSEEGSFAWTHNKSATKPFET
12-1973-2  EETILKNHFQNKFTTLNEDRSAHPNAYKQKSADTLGTLDDFHIAFSEEGSFAWTHNKSATKPFET
11-4503-1  EETILKNHFQNKFTTLNEDRSAHPNAYKQKSADTLGTLDDFHIAFSEEGSFAWTHNKSATKPFET
12-1276-1  EETILKNHFQNKFTTLNEDRSAHPNAYKQKSADTLGTLDDFHIAFSEEGSFAWTHNKSATKPFET
p37rec     EETILKNHFQNKFTTLNEDRSAHPNAYKQKSADTLGTLDDFHIAFSEEGSFAWTHNKSATKPFET 10-3162-1  KANEKMEALIVTNPIPYDVGVFRKSVNQLEQNLIVQTFINLAKNKQDTYGPLLGYNGYKKIDNFQ
11-3945-1  KANEKMEALIVTNPIPYDVGVFRKSVNQLEQNLIVQTFINLAKNKQDTYGPLLGYNGYKKIDNFQ
11-0731-1  KANEKMEALIVTNPIPYDVGVFRKSVNQLEQNLIVQTFINLAKNKQDTYGPLLGYNGYKKIDNFQ
10-1118-4  KANEKMEALIVTNPIPYDVGVFRKSVNQLEQNLIVQTFINLAKNKQDTYGPLLGYNGYKKIDNFQ
09-4107-1  KANEKMEALIVTNPIPYDVGVFRKSVNQLEQNLIVQTFINLAKNKQDTYGPLLGYNGYKKIDNFQ
10-2286-1  KANEKMEALIVTNPIPYDVGVFRKSVNQLEQNLIVQTFINLAKNKQDTYGPLLGYNGYKKIDNFQ
10-1625-1  KANEKMEALIVTNPIPYDVGVFRKSVNQLEQNLIVQTFINLAKNKQDTYGPLLGYNGYKKIDNFQ
12-4130-1  KANEKMEALIVTNPIPYDVGVFRKSVNQLEQNLIVQTFINLAKNKQDTYGPLLGYNGYKKIDNFQ
12-3129-1  KANEKMEALIVTNPIPYDVGVFRKSVNQLEQNLIVQTFINLAKNKQDTYGPLLGYNGYKKIDNFQ
13-00490   KANEKMEALIVTNPIPYDVGVFRKSVNQLEQNLIVQTFINLAKNKQDTYGPLLGYNGYKKIDNFQ
12-4153-1  KANEKMEALIVTNPIPYDVGVFRKSVNQLEQNLIVQTFINLAKNKQDTYGPLLGYNGYKKIDNFQ
12-1416-1  KANEKMEALIVTNPIPYDVGVFRKSVNQLEQNLIVQTFINLAKNKQDTYGPLLGYNGYKKIDNFQ
12-2665-1  KANEKMEALIVTNPIPYDVGVFRKSVNQLEQNLIVQTFINLAKNKQDTYGPLLGYNGYKKIDNFQ
12-1973-2  KANEKMEALIVTNPIPYDVGVFRKSVNQLEQNLIVQTFINLAKNKQDTYGPLLGYNGYKKIDNFQ
11-4503-1  KANEKMEALIVTNPIPYDVGVFRKSVNQLEQNLIVQTFINLAKNKQDTYGPLLGYNGYKKIDNFQ
12-1276-1  KANEKMEALIVTNPIPYDVGVFRKSVNQLEQNLIVQTFINLAKNKQDTYGPLLGYNGYKKIDNFQ
p37rec     KANEKMEALIVTNPIPYDVGVFRKSVNQLEQNLIVQTFINLAKNKQDTYGPLLGYNGYKKIDNFQ 10-3162-1  KEIVEVYEKAIK
11-3945-1  KEIVEVYEKAIK
11-0731-1  KEIVEVYEKAIK
10-1118-4  KEIVEVYEKAIK
09-4107-1  KEIVEVYEKAIK
10-2286-1  KEIVEVYEKAIK
10-1625-1  KEIVEVYEKAIK
12-4130-1  KEIVEVYEKAIK
12-3129-1  KEIVEVYEKAIK
13-00490   KEIVEVYEKAIK
12-4153-1  KEIVEVYEKAIK
12-1416-1  KEIVEVYEKAIK
12-2665-1  KEIVEVYEKAIK
12-1973-2  KEIVEVYEKAIK
11-4503-1  KEIVEVYEKAIK
12-1276-1  KEIVEVYEKAIK
p37rec     KEIVEVYEKAIK
```

*FIG. 6 (Cont'd)*

SEQUENCE LISTING

```
<160> NUMBER OF SEQ ID NOS: 7

<210> SEQ ID NO 1
<211> LENGTH: 27
<212> TYPE: DNA
<213> ORGANISM: Artificial Sequence
<220> FEATURE:
<223> OTHER INFORMATION: p37 Forward Primer

<400> SEQUENCE: 1
gggattgaag tggttgtctg atttaag                                        27

<210> SEQ ID NO 2
<211> LENGTH: 24
<212> TYPE: DNA
<213> ORGANISM: Artificial Sequence
<220> FEATURE:
```

```
<223> OTHER INFORMATION: p37 Reverse Primer

<400> SEQUENCE: 2
caatgaacca gatgcagaac aatc                                              24

<210> SEQ ID NO 3
<211> LENGTH: 33
<212> TYPE: DNA
<213> ORGANISM: Artificial Sequence
<220> FEATURE:
<223> OTHER INFORMATION: p37 Forward Primer

<400> SEQUENCE: 3
gacgacgaca agatgcaggc ctctgcagtc gac                                    33

<210> SEQ ID NO 4
<211> LENGTH: 36
<212> TYPE: DNA
<213> ORGANISM: Artificial Sequence
<220> FEATURE:
<223> OTHER INFORMATION: p37 Reverse Primer

<400> SEQUENCE: 4
gaggagaagc ccggttattt aatcgccttt tcgtag                                 36

<210> SEQ ID NO 5
<211> LENGTH: 460
<212> TYPE: PRT
<213> ORGANISM: Mycobacterium hyorhinis

<400> SEQUENCE: 5
```

Met His His His His His Ser Ser Gly Leu Val Pro Arg Gly Ser
1               5                   10                  15

Gly Met Lys Glu Thr Ala Ala Lys Phe Lys Arg Gln His Met Asp
            20                  25                  30

Ser Pro Asp Leu Gly Thr Asp Asp Asp Lys Met Lys Ala Ser Ala
        35                  40                  45

Val Asp Gly Pro Gly Ile Arg Ser Asn Met Leu Lys Lys Leu Lys Asn
50                  55                  60

Phe Ile Leu Phe Ser Ser Ile Phe Ser Pro Ile Ala Phe Ala Ile Ser
65                  70                  75                  80

Cys Ser Asn Thr Gly Val Val Lys Gln Glu Asp Val Ser Val Ser Gln
                85                  90                  95

Gly Gln Trp Asp Lys Ser Ile Thr Phe Gly Val Ser Glu Ala Trp Leu
            100                 105                 110

Asn Lys Lys Lys Gly Gly Glu Lys Val Asn Lys Glu Val Ile Asn Thr
        115                 120                 125

Phe Leu Glu Asn Phe Lys Lys Glu Phe Asn Lys Leu Lys Asn Ala Asn
    130                 135                 140

Asp Lys Thr Lys Asn Phe Asp Asp Val Asp Phe Lys Val Thr Pro Ile
145                 150                 155                 160

Gln Asp Phe Thr Val Leu Leu Asn Asn Leu Ser Thr Asp Asn Pro Glu
                165                 170                 175

Leu Asp Phe Gly Ile Asn Ala Ser Gly Lys Leu Val Glu Phe Leu Lys
            180                 185                 190

Asn Asn Pro Gly Ile Ile Thr Pro Ala Leu Glu Thr Thr Asn Ser
        195                 200                 205

Phe Val Phe Asp Lys Glu Lys Asp Lys Phe Tyr Val Asp Gly Thr Asp
    210                 215                 220

Ser Asp Pro Leu Val Lys Ile Ala Lys Glu Ile Asn Lys Ile Phe Val
225                 230                 235                 240

Glu Thr Pro Tyr Ala Ser Trp Thr Asp Glu Asn His Lys Trp Asn Gly
            245                 250                 255

Asn Val Tyr Gln Ser Val Tyr Asp Pro Thr Val Gln Ala Asn Phe Tyr
        260                 265                 270

Arg Gly Met Ile Trp Ile Lys Gly Asn Asp Glu Thr Leu Ala Lys Ile
    275                 280                 285

Lys Lys Ala Trp Asn Asp Lys Asp Trp Asn Thr Phe Arg Asn Phe Gly
290                 295                 300

Ile Leu His Gly Lys Asp Asn Ser Phe Ser Lys Phe Lys Leu Glu Glu
305                 310                 315                 320

Thr Ile Leu Lys Asn His Phe Gln Asn Lys Phe Thr Thr Leu Asn Glu
                325                 330                 335

Asp Arg Ser Ala His Pro Asn Ala Tyr Lys Gln Lys Ser Ala Asp Thr
            340                 345                 350

Leu Gly Thr Leu Asp Asp Phe His Ile Ala Phe Ser Glu Glu Gly Ser
        355                 360                 365

Phe Ala Trp Thr His Asn Lys Ser Ala Thr Lys Pro Phe Glu Thr Lys
370                 375                 380

Ala Asn Glu Lys Met Glu Ala Leu Ile Val Thr Asn Pro Ile Pro Tyr
385                 390                 395                 400

Asp Val Gly Val Phe Arg Lys Ser Val Asn Gln Leu Glu Gln Asn Leu
                405                 410                 415

Ile Val Gln Thr Phe Ile Asn Leu Ala Lys Asn Lys Gln Asp Thr Tyr
            420                 425                 430

Gly Pro Leu Leu Gly Tyr Asn Gly Tyr Lys Lys Ile Asp Asn Phe Gln
        435                 440                 445

Lys Glu Ile Val Glu Val Tyr Glu Lys Ala Ile Lys
    450                 455                 460

<210> SEQ ID NO 6
<211> LENGTH: 403
<212> TYPE: PRT
<213> ORGANISM: Mycobacterium hyorhinis

<400> SEQUENCE: 6

Leu Leu Lys Lys Phe Lys Asn Phe Ile Leu Phe Ser Ser Ile Phe Ser
1               5                   10                  15

Pro Ile Ala Phe Ala Ile Ser Cys Ser Asn Thr Gly Val Val Lys Gln
            20                  25                  30

Glu Asp Val Ser Val Ser Gln Gly Gln Trp Asp Lys Ser Ile Thr Phe
        35                  40                  45

Gly Val Ser Glu Ala Trp Leu Asn Lys Lys Gly Asp Lys Glu Val
    50                  55                  60

Asn Lys Glu Val Ile Asn Thr Phe Leu Glu Asn Phe Lys Glu Phe
65                  70                  75                  80

Asn Lys Leu Lys Asn Ala Asn Asp Lys Thr Lys Asn Phe Asp Asp Val
            85                  90                  95

Asp Phe Lys Val Thr Pro Ile Gln Asp Ser Thr Val Leu Leu Asn Asn
            100                 105                 110

Leu Ser Thr Asp Asn Pro Glu Leu Asp Phe Gly Ile Asn Ala Ser Gly
        115                 120                 125

Lys Leu Val Glu Phe Leu Lys Asn Asn Pro Gly Ile Ile Thr Pro Ala

```
                130             135             140
Leu Glu Thr Thr Thr Asn Ser Phe Val Phe Asp Lys Glu Lys Asp Lys
145                 150                 155                 160

Phe Tyr Val Asp Gly Thr Asp Ser Asp Pro Leu Val Lys Ile Ala Lys
                165                 170                 175

Glu Ile Asn Lys Ile Phe Val Glu Thr Pro Tyr Ala Ser Trp Thr Asp
                180                 185                 190

Glu Asn His Lys Trp Asn Gly Asn Val Tyr Gln Ser Val Tyr Asp Pro
                195                 200                 205

Thr Val Gln Ala Asn Phe Tyr Arg Gly Met Ile Trp Ile Lys Gly Asn
210                 215                 220

Asp Glu Thr Leu Ala Lys Ile Lys Lys Ala Trp Asn Asp Lys Asp Trp
225                 230                 235                 240

Asn Thr Phe Arg Asn Phe Gly Ile Leu His Gly Lys Asp Asn Ser Ser
                245                 250                 255

Ser Lys Phe Lys Leu Glu Glu Thr Ile Leu Lys Asn His Phe Gln Asn
                260                 265                 270

Lys Phe Thr Thr Leu Asn Glu Asp Arg Ser Ala His Pro Asn Ala Tyr
                275                 280                 285

Lys Gln Lys Ser Ala Asp Thr Leu Gly Thr Leu Asp Asp Phe His Ile
                290                 295                 300

Ala Phe Ser Glu Glu Gly Ser Phe Ala Trp Thr His Asn Lys Ser Ala
305                 310                 315                 320

Thr Lys Pro Phe Glu Thr Lys Ala Asn Glu Lys Met Glu Ala Leu Ile
                325                 330                 335

Val Thr Asn Pro Ile Pro Tyr Asp Val Gly Val Phe Arg Lys Ser Val
                340                 345                 350

Asn Gln Leu Glu Gln Asn Leu Ile Val Gln Thr Phe Ile Asn Leu Ala
                355                 360                 365

Lys Asn Lys Gln Asp Thr Tyr Gly Pro Leu Leu Gly Tyr Asn Gly Tyr
370                 375                 380

Lys Lys Ile Asp Asn Phe Gln Lys Glu Ile Val Glu Val Tyr Glu Lys
385                 390                 395                 400

Ala Ile Lys

<210> SEQ ID NO 7
<211> LENGTH: 403
<212> TYPE: PRT
<213> ORGANISM: Mycobacterium hyorhinis

<400> SEQUENCE: 7

Leu Leu Lys Lys Phe Lys Asn Phe Ile Leu Phe Ser Ser Ile Phe Ser
1               5                   10                  15

Pro Ile Ala Phe Ala Ile Ser Cys Ser Asn Thr Gly Val Val Lys Gln
                20                  25                  30

Glu Asp Val Ser Val Ser Gln Gly Gln Trp Asp Lys Ser Ile Thr Phe
                35                  40                  45

Gly Val Ser Glu Ala Trp Leu Asn Lys Lys Gly Asp Lys Glu Val
                50                  55                  60

Asn Lys Glu Val Ile Asn Thr Phe Leu Glu Asn Phe Lys Lys Glu Phe
65                  70                  75                  80

Asn Lys Leu Lys Asn Ala Asn Asp Lys Thr Lys Asn Phe Asp Asp Val
                85                  90                  95

Asp Phe Lys Val Thr Pro Ile Gln Asp Ser Thr Val Leu Leu Asn Asn
```

-continued

```
                100                 105                 110
Leu Ser Thr Asp Asn Pro Glu Leu Asp Phe Gly Ile Asn Ala Ser Gly
        115                 120                 125

Lys Leu Val Glu Phe Leu Lys Asn Asn Pro Gly Ile Ile Thr Pro Ala
        130                 135                 140

Leu Glu Thr Thr Thr Asn Ser Phe Val Phe Asp Lys Glu Lys Asp Lys
145                 150                 155                 160

Phe Tyr Val Asp Gly Lys Asp Ser Asp Pro Leu Val Lys Ile Ala Lys
                165                 170                 175

Glu Ile Asn Lys Ile Phe Val Glu Thr Pro Tyr Ala Ser Trp Thr Asp
                180                 185                 190

Glu Asn His Lys Trp Asn Gly Asn Val Tyr Gln Ser Val Tyr Asp Pro
        195                 200                 205

Thr Val Gln Ala Asn Phe Tyr Arg Gly Met Ile Trp Ile Lys Gly Asn
        210                 215                 220

Asp Glu Thr Leu Ala Lys Ile Lys Lys Ala Trp Asn Asp Lys Asp Trp
225                 230                 235                 240

Asn Thr Phe Arg Asn Phe Gly Ile Leu His Gly Lys Asp Asn Ser Ser
                245                 250                 255

Ser Lys Phe Lys Leu Glu Glu Thr Ile Leu Lys Asn His Phe Gln Asn
                260                 265                 270

Lys Phe Thr Thr Leu Asn Glu Asp Arg Ser Ala His Pro Asn Ala Tyr
                275                 280                 285

Lys Gln Lys Ser Ala Asp Thr Leu Gly Thr Leu Asp Asp Phe His Ile
        290                 295                 300

Ala Phe Ser Glu Glu Gly Ser Phe Ala Trp Thr His Asn Lys Ser Ala
305                 310                 315                 320

Thr Lys Pro Phe Glu Thr Lys Ala Asn Glu Lys Met Glu Ala Leu Ile
                325                 330                 335

Val Thr Asn Pro Ile Pro Tyr Asp Val Gly Val Phe Arg Lys Ser Val
                340                 345                 350

Asn Gln Leu Glu Gln Asn Leu Ile Val Gln Thr Phe Ile Asn Leu Ala
        355                 360                 365

Lys Asn Lys Gln Asp Thr Tyr Gly Pro Leu Leu Gly Tyr Asn Gly Tyr
        370                 375                 380

Lys Lys Ile Asp Asn Phe Gln Lys Glu Ile Val Glu Val Tyr Glu Lys
385                 390                 395                 400

Ala Ile Lys
```

ENZYME-LINKED IMMUNOSORBENT ASSAY (ELISA) FOR THE DETECTION OF ANTI-MYCOPLASMA HYORHINIS IGG IN SWINE SERUM

CROSS-REFERENCE TO RELATED APPLICATIONS

This application claims the benefit of priority to U.S. Provisional Application No. 62/088,417 filed Dec. 5, 2014, which is incorporated herein by reference in its entirety.

INCORPORATION BY REFERENCE

All the documents cited herein are incorporated by reference herein in their entirety.

BACKGROUND OF THE INVENTION

Mycoplasma hyorhinis is an important pathogen of swine that can often occur as a respiratory co-infection with viral pathogens[2,3] but has also been shown to cause arthritis and polyserositis in infected animals[4]. The economic impact of disease associated with M. hyorhinis in the United States swine industry has not been evaluated previously. Nonetheless, this organism remains a significant source of infectious disease in commercially raised swine[2,3,4]. Currently, no diagnostic assay is available to assess the degree of exposure to this pathogen in the field, nor is there currently a method which would allow researchers the ability to monitor the serologic response of swine to vaccines administered against this pathogen.

Mycoplasma hyorhinis is an important pathogen in the United States swine industry. Each year infections caused by this pathogen impact the productivity of the swine industry through increased veterinary costs, decreased productivity, and mortality. The Mycoplasma genus consists of small, fastidious organisms of about 0.1 µM in size and lack cell wall[6]. A number of pathogenic species of Mycoplasma that have been shown to infect swine and induce significant lesions upon infection including M. hyopneumoniae, M. hyorhinis, and M. hyosynoviae[7,8]. M. hyopneumoniae is a major cause of respiratory illness in swine, especially as a secondary infection with Porcine circovirus type 2[2] and Porcine Reproductive and Respiratory Syndrome Virus[3]. M. hyosynoviae has been shown to cause of severe arthritis in the joints of infected animals and has also induces a carrier state in the tonsils of pigs[9,10]. M. hyorhinis is pathogenic to both swine and humans[7,11]. In humans, M. hyorhinis has been implicated as a causative agent in gastric carcinoma[11] and prostate cancer[1,12], though it is not a common cause of classical infectious disease.

In swine, the organism can be a found as a commensal resident of the nasal cavity and respiratory tract[14] and virulence and pathogenicity have been shown to vary amongst strains[13]. When a pathogenic strain infects an animal the most common clinical signs are severe arthritis and polyserositis. Occasionally animals may develop otitis and conjunctivitis as a result of infection as well[13]. Treatment options include tetracycline, fluoroquinolone, and macrolide antibiotics as well as tylosin and a number of other antimicrobials[8].

Very little research has been done to determine what specific factors make some strains of M. hyorhinis virulent while others remain non-pathogenic. A significant source of variability in M. hyorhinis strains is the variable lipoproteins (VLPs) that constitute the major membrane proteins expressed by the organism[16,17]. VLPs can change over the course of an infection via a mechanism involving phase variation, differential regulation in expression of multiple VLPs, and changes in VLP size due to the gain or loss of repetitive sequences encoding groups of amino acids 12-13 residues in length[18]. These mechanisms can be used as a means of continuously escaping the host immune system as immunity directed against these proteins can become irrelevant when the population shifts to the use of a new VLP[19]. Another potential source of virulence in M. hyorhinis strains is the ability of at least some strains to modulate the immune response. Previous studies have demonstrated that M. hyorhinis has the ability to suppress IL-2 production in murine T-cells[21] and T-cell activation by mesenchymal stem cells in rats[22].

M. hyorhinis p37 is a 43.5 kD membrane spanning protein that is thought to function in thiamine pyrophosphate binding[23] and in adherence to host cells (cite). Its role in aggravating human gastric cancers is thought to be a result of its activation of matrix metalloprotease 2 (MMP2) and activation of the phosphorylation of epidermal growth factor receptor[20]. M. hyorhinis p37 is thought to bind to sialic acid on the surface of cells via a carboxy-terminal jelly-roll motif[24] and binding of p37 to cancer cells has been shown to facilitate increased invasiveness and metastases[24,20]. One relevant assay uses human sera to determine whether a link exists between M. hyorhinis and prostate cancer,[1] but prior to the instant disclosure, it was not known whether M. hyorhinis p37 could be used to diagnose exposure to M. hyorhinis via vaccination or natural infection.

SUMMARY OF THE INVENTION

In one aspect, the invention provides an Enzyme-Linked Immunosorbent Assay (ELISA) for the selective detection of anti-Mycoplasma hyorhinis IgG in porcine serum, which may contain antibodies specific to multiple other Mycoplasma spp.

In another aspect, the invention provides methods of selectively detecting the presence of Mycoplasma hyorhinis in a biological samples, even where the biological species also contains antibodies specific to multiple other Mycoplasma spp.

In yet a third aspect, the invention provides a method of producing a selective ELISA kit, which yields a positive result for Mycoplasma hyorhinis, despite the presence of antibodies from other Mycoplasma spp.

BRIEF DESCRIPTION OF THE DRAWINGS

This trial was done to verify that animals vaccinated with *M. hyosynoviae* would not seroconvert against the p37 antigen, which was used in the *M. hyorhinis* assay. The results show that serum from animals vaccinated with the *M. hyosynoviae* antigen do not react positively in the *M. hyorhinis* test;

FIG. 5 is a graph showing the mean S/P response for animals vaccinated with *M. hyorhinis* (isolate 10-1625-1), at varied dose levels and formulated with varied adjuvants. Groups: A) $3.998 \times 10^8$, 10% Trigen; B) $3.998 \times 10^7$, 10% Trigen; C) $3.998 \times 10^6$, 10% Trigen; D) $3.998 \times 10^8$, 10% TS6; E) $3.998 \times 10^7$, 10% TS6; F) $3.998 \times 10^6$, 10% TS6; G) $3.998 \times 10^8$, 66% TS6; H) $3.998 \times 10^7$, 66% TS6; I) $3.998 \times 10^6$, 66% TS6; W) $1.06 \times 10^8$ non-concentrated, 10% Trigen; X) $1.06 \times 10^7$ non-concentrated, 10% Trigen; Y) $1.06 \times 10^6$ non-concentrated, 10% Trigen; and J) Controls. The results show that an optimal response is obtained using TS6 at 66% volume. A dose titration can clearly be seen across dose level in every set of adjuvant groups. This result demonstrates the ability of the test to measure the magnitude of the immune response against the antigen.

FIG. 6 ClustalW alignment of p37 sequences from *M. hyorhinis* strains versus the sequence of the p37-His recombinant protein. This alignment shows that the p37 antigen is conserved amongst different strains and shares homology with the disclosed recombinant protein.

DETAILED DESCRIPTION OF THE INVENTION

In the work disclosed herein a related approach was used to determine if p37 could be used as a diagnostic marker for measuring exposure to *M. hyorhinis* through both vaccination and natural exposure in swine. Previous studies have shown that the protein bears some similarity to other proteins present in *Mycoplasma* species[15] and Influenza A virus hemagglutinin[24] at the amino acid and structural levels. In the present disclosure, the p37 protein was used as a means of measuring the IgG response of swine to vaccination with inactivated, whole cell *M. hyorhinis* vaccines derived from three different strains of the pathogen. The assay was further validated to ensure that results of the test would not be confounded by vaccination with either *M. hyopneumoniae* or *M. hyosynoviae*. Finally, the assay was used to estimate the degree of exposure that might be encountered when testing animals in the field in order to get an idea as to the prevalence of this pathogen on a typical farm.

In particular, recombinantly expressed *M. hyorhinis* p37 protein was used to monitor exposure to the pathogen in the field as well as the magnitude of the IgG response in vaccinated animals. The results indicated that the assay had a high degree of specificity in terms of its ability to distinguish animals vaccinated with *M. hyorhinis* versus other important *Mycoplasma* species, for example, *M. hyopneumoniae* and *M. hyosynoviae*. Vaccines used to protect animals against this pathogen appear to induce a strong antibody response against the p37 protein. Additionally, the degree of field prevalence determined using the ELISA in the swine herds tested ranged from 27% to as high as 67%.

Definitions

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., 1984; Geysen et al., 1986. Similarly, conformational epitopes are readily identified by determining spatial conformation of amino acids such as by, e.g., x-ray crystallography and 2-dimensional nuclear magnetic resonance. See, e.g., Epitope Mapping Protocols, supra. Methods especially applicable to the proteins of *T. parva* are fully described in PCT/US2004/022605 incorporated herein by reference in its entirety.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle, calves, steers, bulls), porcine (e.g., pig), avian (e.g., chicken, duck, goose, turkey, quail, pheasant, parrot, finches, hawk, crow, ostrich, emu and cassowary), primate (e.g., prosimian, tarsier, monkey, gibbon, ape), ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Embodiments

In an embodiment, the invention provides a purified, recombinant, non-naturally occurring, non-post-translationally modified, *Mycoplasma hyorhinis* (*M. hyorhinis*) p37 polypeptide having a sequence with at least 98% identity to the sequence as set forth in SEQ ID NO:5; wherein the polypeptide is useful for the selective detection of *M. hyorhinis* antibodies.

In an embodiment, the polypeptide of has the sequence as set forth in SEQ ID NO:5.

In another embodiment, the invention provides an Enzyme-Linked Immunosorbent Assay kit comprising the *M. hyorhinis* polypeptide disclosed herein.

In another aspect of the invention, there is provided a method for making an ELISA plate, for use as a component of the disclosed ELISA kit, comprising the following steps:
 a) suspending the polypeptide in carbonate/bicarbonate buffer to a concentration of about 80 μg/mL to about 120 μg/mL, to produce a coating solution;
 b) adding from about 80 μL to about 120 μL of the coating solution to each well;
 c) incubating the plate for at least about 12 hours at about 4° C.;
 d) removing the coating solution;
 e) blocking the plate;
 f) washing the plate; thereby preparing the ELISA assay plate.

In another embodiment, the invention provides a method for selectively detecting the presence of *M. hyorhinis* in a sample comprising the following steps:
 a) providing the ELISA plate of claim 4;
 b) providing at least an experimental sample, at least one negative control sample, and at least one sample containing antibodies specific to at least one *Mycoplasma* species other than *M. hyorhinis*;
 c) diluting the sample(s) in blocking buffer;
 d) adding an amount of diluted sample(s) into the wells of the plate;
 e) incubating the plates;
 f) washing the wells of the plates to remove the diluted sample(s);
 g) developing the plates using a chromogen;
 h) stopping the chromogen reaction;
 i) reading the plate at a wavelength appropriate for the chromogen used;

j) collecting and recording the absorbance data for the wells;

k) determining that *M. hyorhinis* is present where the sample has significantly more absorbance than the negative control samples; thereby selectively detecting the presence of *M. hyorhinis* in the sample(s).

In yet another embodiment, the invention provides a method for selectively detecting the presence of *M. hyorhinis* P37 antibodies in a test sample, comprising the steps of:

a) providing a test sample suspected of containing P37 antibodies;

b) adding a quantity of the polypeptide to the test sample, the quantity being sufficient to produce a detectable level of binding activity by anti-P37 antibodies in the test sample; and c) detecting the presence of P37 antibodies bound to said polypeptide in the test sample.

In another embodiment, the invention provides a method for selectively detecting the presence of *M. hyorhinis* P37 antibodies in a test sample, comprising the steps of:

a) providing a test sample suspected of containing P37 antibodies;

b) adding a quantity of an immunogenic fragment of the polypeptide to the test sample, the quantity being sufficient to produce a detectable level of binding activity by anti-P37 antibodies in the test sample; and c) detecting the presence of P37 antibodies bound to said polypeptide in the test sample.

A diagnostic kit for the selective diagnosis of the presence in a biological sample of *M. hyorhinis* P37 antibodies; wherein even if the biological sample contains *M. hyosynoviae* and *M. hyopneumoniae* antibodies against orthologous, homologous or paralogous P37, the kit will not yield a positive result unless *M. hyorhinis* antibodies are present. In an embodiment, this kit contains the polypeptide having the sequence as set forth in SEQ ID NO:5.

In still another embodiment, the invention provides a method of detecting exposure to *M. hyorhinis* in an animal or in a biological sample from said animal, comprising the step of detecting the presence or absence of an immune response to the polypeptide having the amino acid sequence shown as SEQ ID NO:5.

EXAMPLES

Example 1

Materials and Methods
Analysis of p37 Gene Sequences:

The *M. hyorhinis* p37 gene sequence was translated in Clone Manager and a BLASTP[26] search was performed against the NCBI "nr" database. All proteins with maximum identity greater than or equal to 35% are reported in Table 1.

TABLE 1

| *Mycoplasma* sp. | Protein Name | Coverage | Max Identity | NCBI Accession |
| --- | --- | --- | --- | --- |
| *M. conjunctivae* | P37-like ABC transporter | 98% | 44% | YP 002960563.1 |
| *M. ovipneumoniae* | DNA repair protein HhH-GDP | 98% | 38% | WP 010321138.1 |
| *M. flocculare* | P37-like ABC transporter substrate-binding protein | 95% | 39% | WP 002557691.1 |
| *M. pulmonis* | P37-like ABC transporter substrate-binding protein | 98% | 39% | NP 326056.1 |
| *M. hyopneumoniae* | P37-like ABC transporter substrate-binding lipoprotein | 93% | 40% | YP 287754.1 |
| *M. genitalium* | alkylphosphate ABC transporter substrate-binding protein | 64% | 39% | YP 006600321.1 |
| *M. arginini* | alkylphosphate ABC transporter substrate-binding component | 65% | 40% | WP 004416279.1 |
| *M. penetrans* | high affinity transport system protein | 80% | 35% | NP 0758050.1 |
| *M. hominis* | ABC transporter substrate-binding lipoprotein | 82% | 38% | YP 003302899.1 |
| *M. gallisepticum* | HatA | 63% | 41% | YP 006581118.1 |
| *M. anatis* | high affinity transport system protein p37 | 61% | 40% | WP 006886440.1 |
| *M. pneumoniae* | high affinity transport system protein p37 | 63% | 37% | YP 005175657.1 |
| *M. iowae* | high affinity transport system protein p37 | 72% | 36% | WP 004025038.1 |
| *M. alkalescens* | P37-like ABC transporter substrate-binding lipoprotein | 64% | 36% | WP 002881335.1 |

Sequencing p37 Genes from *M. hyorhinis* Isolates:

*M. hyorhinis* strains were inoculated into *Mycoplasma* culture medium and grown for three days at 37° C. A 10 mL volume of each culture was then centrifuged at 7500×G for 20 minutes in order to pellet cells. Following this centrifugation the supernatant was discarded and genomic DNA was obtained from the cell pellet by phenol:chloroform extraction and ethanol precipitation. Briefly, the cell pellets were resuspended in 1 mL of phosphate buffered saline and 1 mL of a 1:1 mixture of phenol:chloroform was added. The samples were then homogenized by vigorous mixing. Next, phase separation was achieved by centrifuging the samples at 19000×G for one minute. The aqueous phase was removed from each sample and placed into a new tube. Next, an equal volume of chloroform was added to each tube and samples were mixed by hand. Samples were then centrifuged again for 1 minute at 19000×G and the aqueous phase was removed to a new tube. To each sample, a ¹⁄₁₀ volume of 3M sodium acetate was added. Next, three volumes of 100% ethanol were added to each sample and the samples were allowed to incubate on ice for fifteen minutes. Samples were then centrifuged at 14000×G for thirty minutes at 4° C. to pellet the DNA. The supernatant was removed from each tube and pellets were resuspended in 1 mL of 70% v/v ethanol to remove any remaining contaminants. Samples were then centrifuged again at 14000×G for 15 minutes at 4° C. Finally, pellets were resuspended in 10 mM Tris buffer and frozen at −20° C. until they were sent for PCR sequencing. The p37 gene sequences from various isolates listed in table 2 were amplified using the following set of forward and reverse primers; Forward-5' GGGATTGAAGTGGTTGTCTGATTTAAG 3' (SEQ ID NO:1), Reverse-5' CAATGAACCAGATGCAGAACAATC 3' (SEQ ID NO:2). PCR assays were carried out in a final, 25 µl volume with GoTaqH PCR SuperMix (Promega Inc., Madison, Wis., USA) with 0.2 mM of each primer and 10 ng of genomic DNA from each isolate respectively. The PCR cycling conditions consisted of an initial denaturation at 95° C. for 5 min followed by 35 cycles of denaturation at 95° C. for 30 sec, annealing at 55° C. for 30 sec, and extension at 68° C. for 90 sec, and a final elongation at 72° C. for 5 min. All PCR products were visualized after electrophoresis in 1.0% agarose gels run at 7.0 V/cm by staining with ethidium bromide (EtBr) and sequenced by Sanger di-deoxy chain termination method.

TABLE 2

Origin of the isolates used for p37 gene sequence analysis. The isolates were selected from across the United States

| Isolate | SEQ ID NO (p37 Amino Acid) | Location |
| --- | --- | --- |
| 9-4107-1 | 6 | Owatonna, MN |
| 12-1973-2 | 6 | Laurel, NE |
| 12-2665-1 | 6 | Guymon, OK |
| 13-00490-1 | 6 | Dodge Center, MN |
| 10-1625-1 | 6 | Storm Lake, IA |
| 10-2286-1 | 6 | Wesley, IA |
| 10-3162-1 | 6 | Rose Hill, NC |
| 11-0731-1 | 6 | Guymon, OK |
| 11-3945-1 | 6 | Owatonna, MN |
| 12-1416-1 | 6 | Waldorf, MN |
| 12-3129-1 | 6 | Trimont, MN |
| 12-4130-1 | 6 | Albin, WY |
| 12-1276-1 | 7 | Guymon, OK |
| 11-4503-1 | 7 | Faribault, MN |
| 12-4153-1 | 6 | Steen, MN |

Molecular Cloning of p37 Protein:

Sequence information for *M. hyorhinis* p37 was derived from Genbank sequence M37339.1. This sequence was then codon optimized for expression in *E. coli* by changing the start codon to ATG, the tryptophan codons to TGG, such that the resulting gene could be expressed efficiently in an *E. coli* host. A synthetic gene was then synthesized at Genscript (how to site them) and the resulting sequence obtained in a pUC57 vector. The gene was then amplified from the vector using primers p37 F (GACGACGACAAGATGCAGGCCTCTGCAGTCGAC) (SEQ ID NO:3) and p37 R (GAGGAGAAGCCCGGTTATTTAATCGCCTTTTCGTAG) (SEQ ID NO:4) using a standard PCR protocol. Once amplified, the gene was purified from the reaction mixture using a Qiagen PCR clean up kit according to the manufacturer's instructions. The purified gene was then ligated into a pET30-LIC vector according to the manufacturer's instructions. The ligated vector was then transformed into One-Shot Top 10 Electrocompetent cells (Invitrogen) and transformed cells were plated out on selection media (LB agar with KAN 50 µg/mL). Clones were then grown overnight in selective media (LB Broth with KAN 50 µg/mL) and plasmid was harvested using a Qiagen plasmid extraction kit. Purified plasmid from each clone was then screened for the presence of insert using (insert primers specific for vector). Positive clones were selected and sent for sequencing (Operon). The plasmid was then transformed into *E. coli* BL-21 (DE3) cells by electroporation and transformants were selected by overnight incubation on selective media (LB agar with Kan 50 µg/mL)

Expression and Purification of p37 Protein:

A single BL-21 clone was inoculated into 200 mL of (T-BONE—need to get the commercial name) auto-induction media and grown overnight in a shake flask at 37° C. with agitation at 250 rpm. The next day, cells were centrifuged at 5000×G for 25 minutes, and the supernatants discarded. The pellet was then resuspended in 20 mL of a commercial lysis buffer (BPER Thermo Pierce) and gently homogenized by pipetting the suspension up and down over the pellet. Next, DNAse (sigma) was added at a concentration of 20 U/ml and the resulting mixture was allowed to incubate for two hours at room temperature on a Nutator mixing device. The extraction was then centrifuged at 7500×G for 30 minutes. The supernatant was retained for analysis by SDS-PAGE and western blot. The pellet was resuspended in 8M urea and allowed to incubate for two hours at room temperature on a Nutator mixing device. This suspension was then centrifuged again at 7500×G and passed through a 0.2 µm filter to remove any insoluble solids. Prior to purification a sample from the urea and lysis buffer fractions was tested by SDS-PAGE and western blot to determine which fraction the protein had partitioned into. The urea fraction was selected based on the results of this analysis. Next, a 2 mL nickel affinity column was prepared according to methods recommended by the manufacturer using (insert affinity resin& disposable columns Pierce). 10 mLs of equilibration (insert formula for buffer B) buffer was then passed through the column. Next, the entire urea soluble fraction was passed through the column. The column was then washed using 20 mLs of wash buffer (insert formula for buffer C). Finally, the column was eluted using 5 mLs of elution buffer (insert formula for buffer E). The protein concentration of the resulting solution was determined by BCA assay (Thermo Pierce) according to the kit instructions.

SDS-PAGE and Western Blot:

SDS-PAGE and western blot analysis of p37 was performed on two separate gels in parallel. 100 µL samples were mixed with 20 µL of loading buffer (insert Pierce info) and boiled for 5 minutes to reduce and denature the proteins. Next, 10 µL of protein standards (insert pierce info) and 20 µL of boiled sample were loaded onto a 4-20% gradient SDS-PAGE gel (insert pierce info). The gel was then electrophoresed under a constant current of 85V for 90 minutes. Following electrophoresis, the gels were washed in distilled water for 10 minutes to remove residual SDS. One of the two gels was then stained using a Coomassie based commercial protein stain (insert pierce info) for one hour on a table top mixer. Next, the gel was rinsed briefly in distilled water to remove residual stain and then allowed to incubate in distilled water with mixing overnight to destain the gel before visualization. The other gel was used for western blot analysis and was soaked in running buffer (insert tris-glycine buffer) for ten minutes prior to transferring proteins to a nitrocellulose membrane by electrophoresis. The electrophoresis protocol for transferring the proteins from the gel to the membrane consisted of a one hour transfer at 85V. After transfer, the membrane was removed from the gel and allowed to block overnight at 4° C. in a commercial blocking buffer (Pierce). After blocking, the membrane was then incubated with a Ni:HRP conjugate (insert KPL) at a 1/2000 dilution with gentle agitation at 37° C. for one hour. The blot was then rinsed twice in PBS-T at five minutes per wash with gentle agitation before a final rinse in PBS. The membrane was then allowed to develop for approximately three minutes using a metal enhanced DAB substrate (insert pierce info here) before the reaction was stopped by rinsing the blot with distilled water.

ELISA Assay:

Purified *M. hyorhinis* p37 protein was suspended in carbonate/bicarbonate buffer (Sigma) and 100 μl/well was coated onto the surface of Immulon 2HB plates at a concentration of 100 μg/mL. Plates were allowed to incubate overnight at 4° C. and the coating solution was removed prior to blocking plates. Plates were blocked with 300 μL/well of Neptune block (Immunochemistry Technologies LLC) and allowed to incubate for two hours at 37° C. Plates were then washed one time in PBS-T using a plate washer set to aspirate blocking buffer, add 300 μL/well of wash buffer to the plate, and then aspirate the wash buffer. Next, samples, diluted 1/1000 in Superblock, were added to the plate in duplicate in 100 μL volumes and allowed to incubate for one hour at 37° C. Plates were then washed three times in PBS-T using the same volume setting as the first wash. Conjugate (peroxidase labeled goat anti-swine IgG H&L from KPL) was added to the plate at a 1/5000 dilution and allowed to incubate for one hour at 37° C. After the conjugate incubation, plates were washed four times in PBS-T and developed using TMB chromogen (KPL). The chromogen was added at 100 μL/well and allowed to develop for ten minutes at room temperature. The reaction was stopped by the addition of 1N sulfuric acid added to the plate at 100 μL/well. Plates were then read at a wavelength of 450 nm and absorbance data was exported to Excel. In Excel, the mean absorbance of the two Superblock wells was determined and subtracted from that of every other well on the plate. Next, the mean absorbance of the duplicate samples and controls was determined. Finally, the mean absorbance of every sample and the negative control was divided by that of the positive control sera to obtain sample/positive ratios used to determine positive/negative status of the animals.

Example 2

*M. hyosynoviae* and *M. hyopneumoniae* ELISAs:

Optimization ELISA:

Optimal dilutions for coating antigens onto plates and for antisera to be used in the assay were established via a standard checkerboard method. Antisera from trial 1 was then used in the assay to develop positive and negative controls and to establish a positive/negative threshold for use in further testing. Based on the S/P values reported from the vaccinates receiving the undiluted vaccine, and from the non-vaccinated animals, a cut-off of 0.15 S/P was established that reported the minimum number of false positives (1 animal) and no false negatives. A false positive was defined as a non-vaccinate that reacted in the assay with an S/P greater than the cut-off. A false negative was defined as a vaccinate that failed to react in the assay at a level higher than the cut-off. Cut-off values were tested ranging from 1.0 to 0.1 using data from the trial 1 serum set.

Example 3. Animal Trials

Trial 1: *M. hyorhinis* Study

Twenty-four high health animals were obtained from a commercial supplier and housed in a clean facility until they had reached eight weeks of age. Test animals received two vaccinations of inactivated *M. hyorhinis* vaccine formulated at different dose levels using as shown in Table 3. Vaccinations were given at days 0 and 21. Vaccine was delivered IM in a 2 cc dose. Serum samples were obtained from animals at day 35 for testing in the ELISA.

TABLE 3

Figure 2:
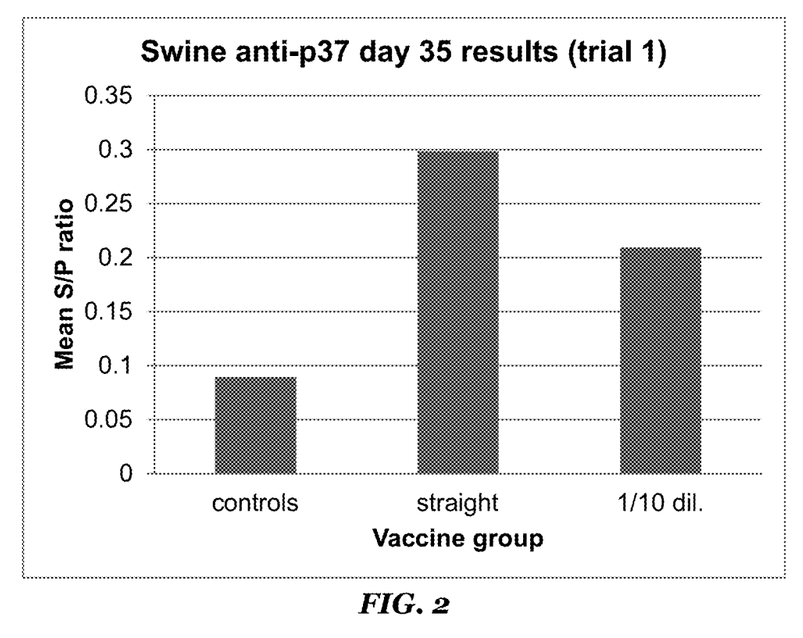
FIG. 2 is a graph showing swine anti-p37 S/P ration at day 35, for the following M. hyorhinis (isolate 10-1625-1) vaccine groups: A) $3.715 \times 10^{\wedge}8$, 10% TRIGEN™; B) $3.715 \times 10^{\wedge}7$, 10% TRIGEN™; C) no treatment. These results show that the disclosed assay was able to differentiate between vaccinated and non-vaccinated animals.

*M. hyorhinis* - Trial 1 (results shown in FIG. 2)

| Group | Treatment | # animals |
|---|---|---|
| A | $3.715 \times 10^8$, 10% Trigen | 10 |
| B | $3.715 \times 10^7$, 10% Trigen | 10 |
| C | no treatment | 4 | isolate 10-1625-1 was used

Trial 2: *M. hyosynoviae* Study

Fifty high health animals were obtained from a commercial supplier and housed in a clean facility until they had reached ten weeks of age. These animals received two vaccinations of inactivated *M. hyosynoviae* vaccine formulated at different dose levels using two different adjuvants as shown in Table 4. Vaccinations were given at days 0 and 21. Vaccine was delivered IM in a 2 cc dose. Serum samples were obtained from animals at days 35 for testing in the *M. hyorhinis* ELISA as well as an *M. hyosynoviae* ELISA similar to one published by Nielsen et al.[28].

TABLE 4

Figure 3:
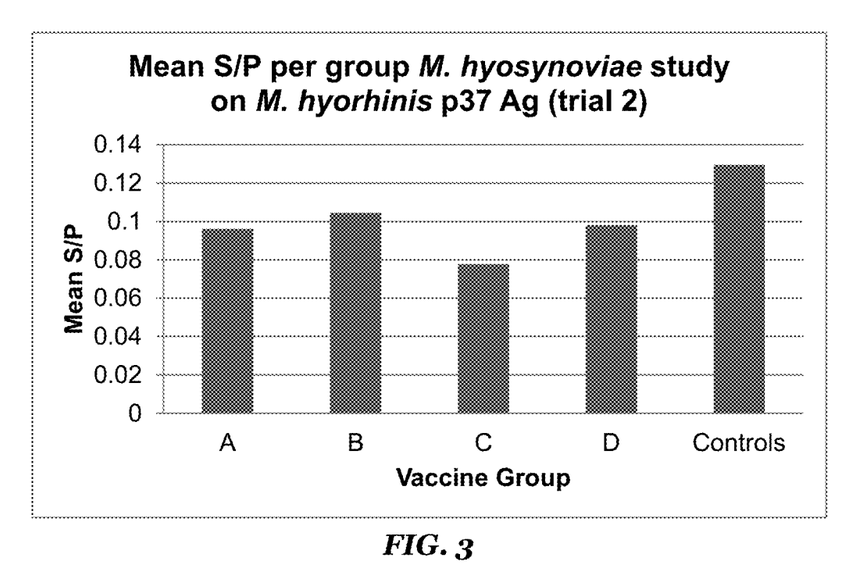
FIG. 3 is a graph showing the mean S/P ratio per group M. hyosynoviae study on M. hyorhinis p37 antigen. The groups were vaccinated as follows: A) $5.012 \times 10^{\wedge}8$, 10% TRIGEN™; B) $5.012 \times 10^{\wedge}8$, 66% TS6; C) $5.012 \times 10^{\wedge}7$, 10% TRIGEN™; D) $5.012 \times 10^{\wedge}7$, 66% TS6; and E) no treatment.

*M. hyosynoviae* - Trial 2 (results shown in FIG. 3)

| Group | Treatment | # animals | # animals tested |
|---|---|---|---|
| A | $5.012 \times 10^8$, 10% Trigen | 10 | 8 |
| B | $5.012 \times 10^8$, 66% TS6 | 10 | 10 |
| C | $5.012 \times 10^7$, 10% Trigen | 10 | 9 |
| D | $5.012 \times 10^7$, 66% TS6 | 10 | 8 |
| E | no treatment | 10 | 9 |

Trial 3: *M. hyopneumoniae* Study:

A serum set containing 40 sera from animals having received either a PCV2 vaccination or a vaccination against *M. hyopneumoniae* was used in the assay. Animals were obtained from a high health herd and vaccinated IM at days 0 and 21 using a 2 cc dose. Animals having received the PCV2 vaccine were considered to be non-vaccinates for the purpose of compiling the results. Animals receiving *M. hyopneumoniae* vaccine were considered to be vaccinates. Serum taken when the animals were 8 weeks of age at day 35 of the study protocol was tested using both a commercially available *M. hyopneumoniae* ELISA and the *M. hyorhinis* ELISA.

TABLE 5

Figure 4:
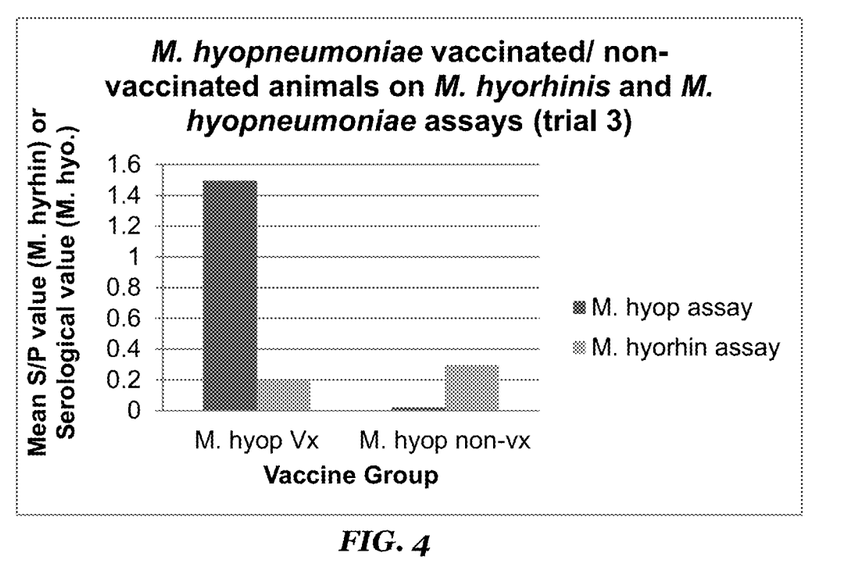
FIG. 4 is a graph showing *M. hyopneumoniae* vaccine/non-vaccinated animals on *M. hyorhinis* and *M. hyopneumoniae* assays. For Group A, twenty animals were given a commercial *M. hyo* vaccine (VACCINE NAME); and for Group B, nineteen animals were given a commercial PCV2 vaccine (CIRCOVAC®). The results show that serum from animals vaccinated with *M. hyopneumoniae* does not react positively in the *M. hyorhinis* test.

*M. hyopneumoniae* - Trial 3 (results shown in FIG. 4)

| Group | Treatment | # animals |
|---|---|---|
| A | *M. hyo* commercial vaccine | 20 |
| B | PCV2 commercial vaccine | 19 |

Trial 4: *M. hyorhinis* Study 2 (Test Set)

One-hundred nineteen high health animals were obtained from a commercial supplier and housed in a clean facility until they had reached ten weeks of age. These animals received two vaccinations of inactivated *M. hyorhinis* vaccine formulated at different dose levels using two different adjuvants as shown in Table 6. Vaccinations were given at days 0 and 21. Vaccine was delivered IM in a 2 cc dose. Serum samples were obtained from animals at days 0, 21, and 35 for testing in ELISA.

TABLE 6

Figure 5:
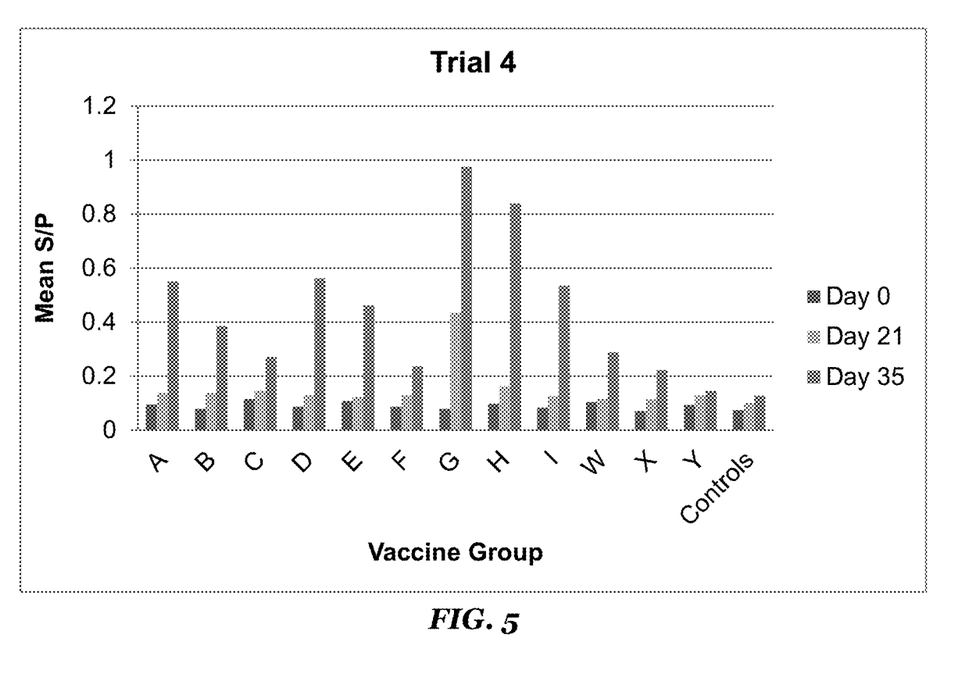

*M. hyorhinis* - Trial 4 (results shown in FIG. 5)

| Group | Treatment | # animals |
|---|---|---|
| A | $3.998 \times 10^8$, 10% Trigen | 10 |
| B | $3.998 \times 10^7$, 10% Trigen | 10 |
| C | $3.998 \times 10^6$, 10% Trigen | 10 |
| D | $3.998 \times 10^8$, 10% TS6 | 10 |
| E | $3.998 \times 10^7$, 10% TS6 | 10 |
| F | $3.998 \times 10^6$, 10% TS6 | 10 |
| G | $3.998 \times 10^8$, 66% TS6 | 9 |
| H | $3.998 \times 10^7$, 66% TS6 | 9 |
| I | $3.998 \times 10^6$, 66% TS6 | 9 |
| W | $1.06 \times 10^8$ non-concentrated, 10% Trigen | 9 |
| X | $1.06 \times 10^7$ non-concentrated, 10% Trigen | 9 |
| Y | $1.06 \times 10^6$ non-concentrated, 10% Trigen | 9 |
| J | Controls | 5 |

Trial 5: Field Prevalence

Two hundred-fifty serum samples that had been submitted to our laboratory for un-related diagnostic testing were used to estimate the sero-prevalence of antibody against the p37 antigen. These samples were obtained from a variety of animals across multiple locations in the United States. Samples were subjected to ELISA testing as described above and the results were compiled in terms of the number of animals testing positive for antibody in the test.

Results

A BLAST search for proteins with homologous to p37 protein used in this study[5] shows that they are highly conserved across *M. hyorhinis* strains. Among the homologs identified during the BLAST analysis one originated from *M. conjunctivae* and one from *M. ovipneumoniae* which have not been previously isolated from swine. However, an *M. conjunctiva* appears to be genetically related to other *Mycoplasma* species that infect swine[25]. A homologous protein from *M. flocculare*, a commensal strain commonly found in swine[27] was also found in the search. Due to the common practice of vaccinating pigs against *M. hyopneumoniae*, interference from vaccination against this pathogen was evaluated in the assay (Table 1).

The *M. hyorhinis* isolates analyzed in this study were taken from geographically dispersed locations and over a four year time period indicating that there has been little temporal drift in the p37 sequence and that even over large geographic distances there is very little difference in the protein sequence between strains. The recombinant protein sequence that was used for the ELISA does contain seven differences in the amino acid sequence when compared to the isolate sequences. However, it is apparent from the reactivity in the ELISA that these do not prevent binding of antibody to the antigen.

Figure 1:
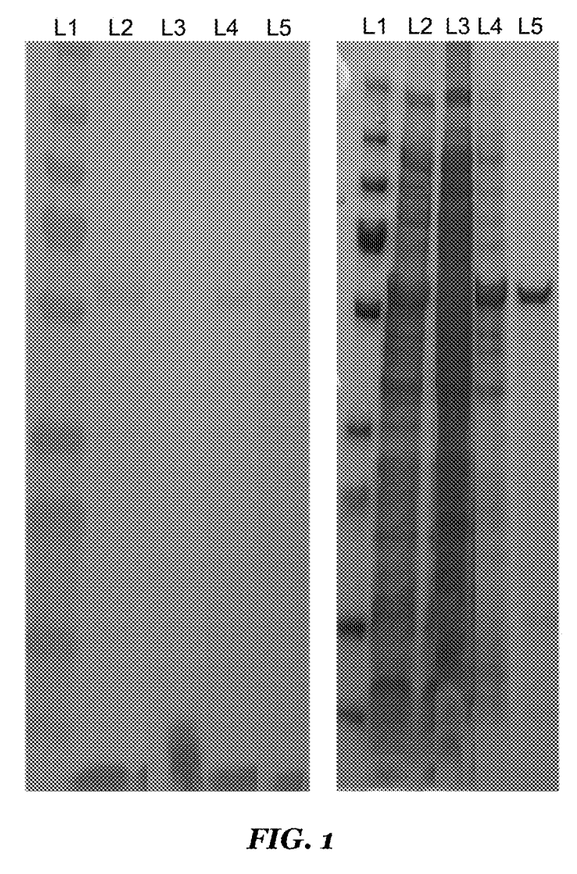
FIG. 1 Western blot and SDS-PAGE gel of recombinant p37 protein fractions. L1: Standard; L2: Whole cell lysate L3: BPER soluble extract L4: Urea soluble extract L5: purified protein. This figure shows how the p37 protein partitions during purification and demonstrates the purity of the final antigen preparation.

The SDS-PAGE gel and western blot show the partitioning of the antigen into inclusion bodies during expression in the *E. coli* host. This was not surprising as p37 is a membrane bound protein and would have been difficult to express in a soluble form. Additionally, purification from the inclusion body phase resulted in a very pure preparation which is important in order to prevent interference in the test from antibodies made against *E. coli* which is likely to be present in swine, particularly in older animals.

The initial proof of concept study that was done to determine whether the p37 assay could detect antibody against *M. hyorhinis* successfully demonstrated that we could detect an immune response in vaccinated animals that was not present in the controls. A later study performed using a dose titration of inactivated *M. hyorhinis* in two different adjuvants demonstrated that we could obtain a more potent response when using a different adjuvant than that used in our initial study. Also, we were able to see the response in the ELISA diminish as the dose of the antigen was decreased, indicating that this assay may have value as a means of semi-quantitatively measuring the immune response as well.

The remaining two trials were performed in order to determine if antibodies made in response to vaccination with other species of *Mycoplasma* that are known to infect swine might interfere with the test. The results of these two trials demonstrate that animals that had been vaccinated with *M. hyosynoviae* and *M. hyopneumoniae* did not react positively in the assay indicating that the assay has sufficient specificity to measure antibody made against *M. hyorhinis* and will not detect antibody against either *M. hyosynoviae* or *M. hyopneumoniae*.

In summary, the p37 antigen can be used as a means to monitor the response to vaccination with inactivated *M. hyorhinis*. The test exhibits a high degree of selectivity toward antibodies made against this species and the p37 protein is well conserved which should allow us to monitor the response against many, if not all, strains currently circulating in the United States. We were also able to measure the magnitude of the immune response using this assay which resulted in an improvement in our inactivated vaccine through the use of a new adjuvant system.

Sources and Manufacturers
 a) Thermo Pierce—3747 N Meridian Rd, Rockford, Ill. 61101
 b) Sigma-Aldrich—3050 Spruce St, St. Louis, Mo. 63103
 c) T-BONE manufacturer—
 d) Kirkegaard & Perry Laboratories—910 Clopper Road, Gaithersburg, Md. 20878
 e) Immunochemistry Technologies LLC—9401 James Avenue South, Suite 155, Bloomington, Minn. 55431
 f) IDEXX—One IDEXX Drive, Westbrook, Me. 04092

REFERENCES

1. Urbanek C, Goodison S, Chang M, et al.: 2011, Detection of antibodies directed at *M. hyorhinis* p37 in the serum of men with newly diagnosed prostate cancer. BMC Cancer 11:233-238.
2. Hansen M S, Pors S E, Jensen H E, et al.: 2010, An investigation of the pathology and pathogens associated with porcine respiratory disease complex in Denmark. J Comp Pathol 143:120-131.
3. Palzer A, Ritzmann M, Wolf G, Heinritzi K: 2008, Associations between pathogens in healthy pigs and pigs with pneumonia. Vet Rec 162:267-271.
4. Kim B, Lee K, Han K, et al.: 2010, Development of in situ hybridization for the detection of *Mycoplasma hyorhinis* in formalin-fixed paraffin-embedded tissues from naturally infected pigs with polyserositis. J Vet Med Sci 72:1225-1227.

5. Dudler R, Schmidhauser C, Parish R W, et al.: 1988, A *mycoplasma* high-affinity transport system and the in vitro invasiveness of mouse sarcoma cells. EMBO J 7:3963-3970.
6. Razin S, Hayflick L: 2010, Highlights of *mycoplasma* research—An historical perspective. Biologicals 38:183-190.
7. Minion F C: 2002, Molecular pathogenesis of *mycoplasma* animal respiratory pathogens. Front Biosci 7:1410-1422.
8. Kobisch M, Friis N F: 1996, Swine mycoplasmoses. Rev Sci Tech 15: 1569-1605.
9. Hagedorn-Olsen T, Nielsen N C, Friis N F, Nielsen J: 1999, Progression of *Mycoplasma hyosynoviae* infection in three pig herds. Development of tonsillar carrier state, arthritis, and antibodies in serum and synovial fluid in pigs from birth to slaughter. Zentralbl Veterinarmed A 46: 555-564.
10. Friis N F, Ahrens P, Larsen H: 1991, *Mycoplasma hyosynoviae* isolation from the upper respiratory tract and tonsils of pigs. Acta Vet Scand 32:425-429.
11. Yang H, Qu L, Chen L, et al.: 2010, *Mycoplasma hyorhinis* infection in gastric carcinoma and its effects on the malignant phenotypes of gastric cancer cells. BMC Gastroenterol 10:132-139.
12. Namiki K, Goodison S, Porvasnik S, et al: 2009, Persistent exposure to *Mycoplasma* induces malignant transformation of human prostate cells. PLoS One 4:e6872.
13. Gois M, Kuksa F: 1974, Intranasal infection of gnotobiotic piglets with *Mycoplasma hyorhinis*: Differences in virulence of the strains and influence of age on the development of infection. Zentralbl Veterinarmed B 21:352-361.
14. Gomes Neto J C, Gauger P C, Strait E L, et al.: 2012, *Mycoplasma*-associated arthritis: Critical points for diagnosis. J Swine Health Prod 20:82-86.
15. Sippel K H, Robbins A H, Reutzel R, et al.: 2009, Structural insights into the extracytoplasmic thiamine-binding lipoprotein p37 of *Mycoplasma hyorhinis*. J Bacteriol 191:2585-2592.
16. Yogev D, Rosengarten R, Watson-McKown R, Wise K S: 1991, Molecular basis of *Mycoplasma* surface antigenic variation: a novel set of divergent genes undergo spontaneous mutation of periodic coding regions and 5' regulatory sequences. EMBO J 10:4069-4079.
17. Rosengarten R, Wise K S: 1990, Phenotypic switching in mycoplasmas: phase variation of diverse surface lipoproteins. Science 247:315-318.
18. Rosengarten R, Wise K S: 1991, The VLP system of *Mycoplasma hyorhinis*: Combinatorial expression of distinct size variant lipoproteins generating high-frequency surface antigenic variation. J Bacteriol 173:4782-4793.
19. Citti C, Kim M F, Wise K S: 1997, Elongated versions of VLP surface lipoproteins protect *Mycoplasma hyorhinis* escape variants from growth-inhibiting host antibodies. Infect Immun 65:1773-1785.
20. Gong M, Meng L, Beihai J, et al.: 2008, p37 from *Mycoplasma hyorhinis* promotes cancer cell invasiveness and metastasis through activation of MMP-2 and followed by phosphorylation of EGFR. Mol Cancer Ther 7:530-537.
21. Teh H S, Ho M, Williams L D: 1988, Suppression of cytotoxic responses by a supernatant factor derived from *Mycoplasma hyorhinis*-infected mammalian cell lines. Infect Immun 56:197-203.
22. Zinocker S, Wang M-Y, Gaustad P, et al.: 2011, *Mycoplasma* contamination revisited: Mesenchymal stromal cells harboring *Mycoplasma hyorhinis* potently inhibit lymphocyte proliferation In Vitro. PLoS ONE 6:e16005.
23. Sippel K H, Robbins A H, Reutzel R, et al.: 2009, Structural insights into the extracytoplasmic thiamine-binding lipoprotein p37 of *Mycoplasma hyorhinis*. J Bacteriol 191:2585-2592.
24. Ketcham C M, Anai S, Reutzel R, et al.: 2005, p37 induces tumor invasiveness. Mol Cancer Ther 4:1031-1038.
25. Liu W, Fang L, Li M, et al.: 2012, Comparative genomics of *Mycoplasma*: Analysis of conserved essential genes and diversity of the pan-genome. PLoS ONE 7:e35698.
26. Stephen F, Altschul T L, Madden A A, et al.: 1997, Gapped BLAST and PSI-BLAST: a new generation of protein database search programs. Nucleic Acids Res 25: 3389-3402.
27. Armstrong C H, Sands-Freeman L, Freeman M J: 1987, Serological, pathological, and cultural evaluations of swine infected experimentally with *Mycoplasma flocculare*. Can J Vet Res 51:185-188.
28. Nielsen E O, Lauritsen K T, Friis N F, et al.: 2005, Use of a novel serum ELISA method and the tonsil-carrier state for evaluation of *Mycoplasma hyosynoviae* distributions in pig herds with or without clinical arthritis. Vet Microbiol 111:41-5

What is claimed:

1. A purified, recombinant, non-naturally occurring, non-post-translationally modified, *Mycoplasma hyorhinis* (*M. hyorhinis*) p37 polypeptide having a sequence with at least 98% identity to the sequence as set forth in SEQ ID NO:5; wherein the polypeptide is useful for the selective detection of *M. hyorhinis* antibodies.

2. The polypeptide of claim 1, wherein the polypeptide has the sequence as set forth in SEQ ID NO:5.

3. An Enzyme-Linked Immunosorbent Assay kit comprising the polypeptide of claim 1.

4. A method for making an ELISA plate, for use as a component of the kit of claim 3, comprising the following steps:

a) suspending the polypeptide of claim 1 in carbonate/bicarbonate buffer to a concentration of about 80 μg/mL to about 120 μg/mL, to produce a coating solution;

b) adding from about 80 μL to about 120 μL of the coating solution to each well;

c) incubating the plate for at least about 12 hours at about 4° C.;

d) removing the coating solution;

e) blocking the plate;

f) washing the plate; thereby preparing the ELISA assay plate.

* * * * *